United States Patent [19]

Desmurs et al.

[11] Patent Number: 4,954,662

[45] Date of Patent: Sep. 4, 1990

[54] SELECTIVE CHLORINATION OF ORTHO-SUBSTITUTED PHENOLS

[75] Inventors: Jean-Roger Desmurs, Saint-Symphorien d'Ozon; Bernard Besson, Pont de Claix; Isabelle Jouve, Villeubanne, all of France

[73] Assignee: Rhone-Poulenc Chimie, Courbevoie, France

[21] Appl. No.: 220,254

[22] Filed: Jul. 18, 1988

[30] Foreign Application Priority Data

Jul. 17, 1987 [FR] France ................................ 87 10417

[51] Int. Cl.$^5$ ...................... C07C 37/62; C07C 39/24
[52] U.S. Cl. ................................... 568/779; 568/650; 568/709; 568/774; 568/776
[58] Field of Search ............... 568/650, 709, 774, 776, 568/779

[56] References Cited

U.S. PATENT DOCUMENTS

| | | | |
|---|---|---|---|
| 3,988,369 | 10/1976 | Pearson | 568/779 |
| 4,160,114 | 7/1979 | Shelton et al. | 568/779 |
| 4,210,766 | 7/1980 | Sollo et al. | 568/774 |
| 4,237,321 | 12/1980 | Cutherbton | 568/779 |
| 4,284,830 | 8/1981 | Knudsen et al. | 568/774 |
| 4,827,047 | 5/1989 | Desmurs et al. | 568/709 |

FOREIGN PATENT DOCUMENTS

| | | | |
|---|---|---|---|
| 0196260 | 12/1983 | European Pat. Off. | 568/774 |
| 2632565 | 2/1978 | Fed. Rep. of Germany | 568/779 |
| 3318791 | 12/1983 | Fed. Rep. of Germany | 568/779 |
| 2307785 | 12/1986 | France | 568/779 |

*Primary Examiner*—Werren B. Lone
*Attorney, Agent, or Firm*—Burns, Doane, Swecker & Mathis

[57] ABSTRACT

Ortho-substituted phenolic compounds, e.g., 2,6-dichlorophenol, are selectively chlorinated, e.g., into 2,4,6-trichlorophenol, with gaseous chlorine in either the molten state or in a solvent medium, in the presence of a selectivity-enhancing effective amount of an organic cation.

18 Claims, No Drawings

SELECTIVE CHLORINATION OF ORTHO-SUBSTITUTED PHENOLS

CROSS-REFERENCE TO COMPANION APPLICATIONS

Our copending applications, Ser. Nos. 220,729 and 219,780 both filed concurrently herewith and both assigned to the assignee hereof.

BACKGROUND OF THE INVENTION

1. Field of the Invention

The present invention relates to the selective chlorination with gaseous chlorine of phenolic compounds which are substituted in the ortho positions with respect to the hydroxyl group.

2. Description of the Prior Art

Among the more important phenolic compounds which can be produced by chlorination of a phenolic compound which is substituted in the ortho positions, notable is 2,4,6-trichlorophenol.

The usual process for the preparation of 2,4,6-trichlorophenol consists of chlorinating 2,4-dichlorophenol.

However, a low proportion of 2,4,5-trichlorophenol is formed (on the order of 0.003 to 0.010% by weight of 2,4,6-trichlorophenol). 2,4,6-Trichlorophenol, which is an intermediate for the synthesis of other compounds, must contain only minimum trace amounts of this undesirable isomer.

Need therefore exists for processes enabling the chlorination of 2,6-dichlorophenol, which would totally avoid the formation of 2,4,5-trichlorophenol. 2,3,6-Trichlorophenol, which is the more likely to be formed in this case in trace amounts, is much less problematical than 2,4,5-trichlorophenol.

Indeed, when 2,6-dichlorophenol is chlorinated using gaseous chlorine, it is observed that an excellent yield is not obtained. In particular, a large amount of 2,4,5,6,6-pentachlorocyclo-2-hexenone is formed, which renders the reaction mixture very unstable and difficult to purify.

Cf. U.S. Pat. Nos. 4,160,114 and 4,223,166, FR-A-2,307,785, FR-A-2,584,068, *Patent Abstracts of Japan*, 11, No. 43 (C-402) [2490], Feb. 7, 1987, and JP-A-61/207,351.

SUMMARY OF THE INVENTION

Accordingly, a major object of the present invention is the provision of an improved process for the para-chlorination, in good yields, of phenolic compounds having substituents in the ortho positions with respect to the hydroxyl group.

Briefly, the present invention features the chlorination of phenolic compounds having the general formula (I):

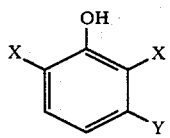

in which:
the symbols X, which may be identical or different, are each a chlorine atom, a bromine atom, a methyl or ethyl group, a methoxy or ethoxy group, an acetoxy group, an $NO_2$ group or an acylamino group having 1 to 4 carbon atoms; and
the symbol Y is a hydrogen atom, a methyl or ethyl group, a methoxy or ethoxy group; and which comprises conducting the chlorination reaction, using gaseous chlorine, in the presence of a selectivity-enhancing effective amount of at least one organic cation.

DETAILED DESCRIPTION OF THE PREFERRED EMBODIMENTS OF THE INVENTION

More particularly according to the present invention, either a single organic cation or a mixture of several different organic cations can be employed.

By the term "organic cation", as utilized herein, are intended the onium ions which are derived especially from nitrogen, from phosphorus, from arsenic, from sulfur, from selenium, from oxygen, from carbon or from iodine and which are coordinated with hydrocarbon moieties. The onium ions which are derived from nitrogen, from phosphorus or from arsenic will be tetracoordinated, the onium ions which are derived from sulfur, from selenium, from oxygen, from carbon, or from S=O will be tricoordinated, while the onium ions which are derived from iodine will be dicoordinated.

The hydrocarbon moieties which are coordinated with these different elements are alkyl, alkenyl, aryl, cycloalkyl and aralkyl radicals which can optionally be substituted, with the proviso that 2 coordinated hydrocarbon moieties may together form a single divalent radical.

The nature of the anions which are associated with these organic cations is not of critical importance. All of the "hard" or "borderline" bases are suitable as the anion.

The terms "hard" or "borderline" connote any anion having the classical definition given by R. Pearson in *Journal of Chem. Ed.*, 45, pages 581–587 (1968).

Exemplary onium ions which can be used in the present chlorination process are those having the following general formulae:

in which:
Z is N, P or As;

Y is S, O, Se, S=O or C;

$R^6$, $R^7$, $R^8$ and $R^9$, which may be identical or different, are each a straight or branched chain alkyl radical which has 1 to 16 carbon atoms and can optionally be substituted by one or more phenyl groups, hydroxyl groups, halogen groups, nitro groups, alkoxy or alkoxycarbonyl groups, the alkoxy groups having 1 to 4 carbon atoms; a straight or branched chain alkenyl radical having 2 to 12 carbon atoms; an aryl radical which has 6 to 10 carbon atoms and can optionally be substituted by one or more alkyl groups having 1 to 4 carbon atoms, alkoxy groups or alkoxycarbonyl groups, the alkoxy radical having 1 to 4 carbon atoms, or halogen atoms, with the proviso that two of said radicals $R_6$ to $R_9$ may together form an alkylene, alkenylene or alkadienylene radical, which can be straight or branched chain and has from 3 to 6 carbon atoms;

$R_{10}$, $R_{11}$, $R_{12}$, $R_{13}$, which may also be identical or different, are each a straight or branched chain alkyl radical containing from 1 to 4 carbon atoms, with the proviso that the radicals $R_{12}$ and $R_{13}$ may together form an alkylene radical containing from 3 to 6 carbon atoms, and the radicals $R_{11}$ and $R_{12}$ or $R_{11}$ and $R_{13}$ may together form an alkylene, alkenylene or alkadienylene radical, containing 4 carbon atoms and, with the nitrogen atom, constitute a nitrogen-containing heterocycle;

$R_{14}$ is a divalent radical forming with the 2 nitrogen atoms a ring member which has 4 to 6 atoms and optionally containing one or more nitrogen, sulfur and/or oxygen heteroatoms, with the proviso that such heterocycle may be substituted by one or more radicals such as $R_6$.

Among the "hard" or "borderline" bases which can form the anion of said onium salts, representative are the ions: $F^-$, $ClO^-_4$, $PF^-_6$, $BF^-_4$, $SnCl^-_6$, $SbCl^-_6$, $B(Ph)^-_4$, $PO^{3-}_4$, $HPO^{2-}_4$, $H_2PO^-_4$, $CH_3SO^-_3$, $PhSO^-_3$, $HSO^-_4$, $NO^-_3$, $SO^{2-}_4$, $Cl^-$, $Br^-$, $I^-$, $OH^-$, with Ph denoting a phenyl radical, as well as all the other anions corresponding to Pearson's definition of "hard" or "borderline" base.

For reasons of convenience of use, preferred such anions are $PO^{3-}_4$, $HPO^{2-}_4$, $H_2PO^-_4$, $CH_3SO^-_3$, $PhSO^-_3$, $NO^-_3$, $SO^{2-}_4$, $PF^-_6$, $Cl^-$, $Br^-$, $I^-$, with Ph being defined as above. The anions $Cl^-$ and $Br^-$, and more especially the anion $Cl^-$, are advantageously used.

Exemplary of the organic cations corresponding to the formula (II), representative are the cations:
tetramethylammonium,
triethylmethylammonium,
tributylmethylammonium,
trimethylpropylammonium,
tetraethylammonium,
tetrabutylammonium,
dodecyltrimethylammonium,
methyltrioctylammonium,
heptyltributylammonium,
tetrapropylammonium,
tetrapentylammonium,
tetrahexylammonium,
tetraheptylammonium,
tetraoctylammonium,
tetradecylammonium,
butyltripropylammonium,
methyltributylammonium,
pentyltributylammonium,
methyldiethylpropylammonium,
ethyldimethylpropylammonium,
tetradodecylammonium,
tetraoctadecylammonium,
hexadecyltrimethylammonium,
benzyltrimethylammonium,
benzyldimethylpropylammonium,
benzyldimethyloctylammonium,
benzyltributylammonium,
benzyltriethylammonium,
phenyltrimethylammonium,
benzyldimethyltetradecylammonium,
benzyldimethylhexadecylammonium,
dimethyldiphenylammonium,
methyltriphenylammonium,
2-butenyltriethylammonium,
N,N-dimethyltetramethyleneammonium,
N,N-diethyltetramethyleneammonium,
tetramethylphosphonium,
tetrabutylphosphonium,
ethyltrimethylphosphonium,
trimethylpentylphosphonium,
octyltrimethylphosphonium,
dodecyltrimethylphosphonium,
trimethylphenylphosphonium,
diethyldimethylphosphonium,
dicyclohexyldimethylphosphonium,
dimethyldiphenylphosphonium,
cyclohexyltrimethylphosphonium,
triethylmethylphosphonium,
methyltri(isopropyl)phosphonium,
methyltri(n-propyl)phosphonium,
methyltri(n-butyl)phosphonium,
methyltri(2-methylpropyl)phosphonium,
methyltricyclohexylphosphonium,
methyltriphenylphosphonium,
methyltribenzylphosphonium,
methyltri(4-methylphenyl)phosphonium,
methyltrixylylphosphonium,
diethylmethylphenylphosphonium,
dibenzylmethylphenylphosphonium,
ethyltriphenylphosphonium,
tetraethylphosphonium,
ethyltri(n-propyl)phosphonium,
triethylpentylphosphonium,
hexadecyltributylphosphonium,
ethyltriphenylphosphonium,
n-butyltri(n-propyl)phosphonium,
butyltriphenylphosphonium,
benzyltriphenylphosphonium,
(β-phenylethyl)dimethylphenylphosphonium,
tetraphenylphosphonium,
triphenyl(4-methylphenyl)phosphonium,
tetrakis(hydroxymethyl)phosphonium,
tetraphenylarsonium.

Exemplary of the cations corresponding to the formulae (III) and (III'), representative are:
N-methylpyridinium,
N-ethylpyridinium,
N-hexadecylpyridinium,
N-methylpicolinium,
1,2,4-triphenyltriazolium.

Exemplary of the organic cations corresponding to the formula (IV), representative are:
trimethylsulfonium,
triethylsulfonium,
triphenylsulfonium,
trimethylsulfoxonium,
triphenylcarbenium, triethyloxonium.

Exemplary of the organic cations corresponding to the formula (V), representative are:
diphenyliodonium,
4,4'-dimethoxydiphenyliodonium (or the compounds described in JACS, 81, 342 (1958)),
diphenyliodonium-2-carboxylate.

Among the organic cations which are useful according to the process of this invention, the quaternary ammonium ions, quaternary phosphonium ions, sulfonium ions and iodonium ions will most typically be the preferred.

The onium salt may be introduced in the solid state, or in the form of a solution in one of the solvents therefor, typically water.

The process according to the invention may be carried out in the absence of solvent: the reagents are then in molten state. This alternative embodiment of the invention typically provides the best results.

The reaction can also be conducted in a liquid medium, especially in an aliphatic ether, an aliphatic hydrocarbon, a chlorinated aliphatic hydrocarbon, a chlorobenzene or a bromobenzene, or a carboxylic acid.

Preferred aliphatic ethers are dipropyl oxide, diisopropyl oxide, methyl and tert-butyl oxide.

Preferred aliphatic hydrocarbons are hexane, heptane, octane, nonane and decane.

Preferred chlorinated hydrocarbons are perchlorinated hydrocarbons such as, in particular, carbon tetrachloride, tetrachloroethylene, hexachloroethane, hexachloropropene and hexachlorobutadiene; also representative are the partially chlorinated hydrocarbons such as methylene chloride, dichloroethane, tetrachloroethane, trichloroethylene, 1-chlorobutane and 1,2-dichlorobutane.

Preferred chlorobenzenes are monochlorobenzene, 1,2-dichlorobenzene, 1,3-dichlorobenzene, 1,4-dichlorobenzene or mixtures of various chlorobenzenes; preferred bromobenzenes are monobromobenzene or mixtures of monobromobenzene with one or more dibromobenzenes.

And the preferred carboxylic acids are acetic acid and propionic acid.

When the process of the invention is carried out in a solvent medium, the concentration of the chlorophenol of formula (I) in the solvent is not critical. It will depend especially on the solubility of the chlorophenol in the solvent used.

The amount of organic cation used in the process of the invention may vary over very wide limits.

It usually constitutes 0.005% to 25% by weight of onium salt relative to the weight of the phenolic compound of formula (I).

When the reaction is carried out in the molten state, it is preferred to use 0.015% to 5% by weight of onium salt relative to the phenolic compound of formula (I) in order to be sufficiently effective, without having an excessive amount of onium salt.

When the reaction is carried out in a solvent medium, it will be preferable to use 5 to 25% by weight of onium salt relative to the phenolic compound of formula (I). In this case, it is preferable to express the amount of onium salt relative to the reaction mixture. For example, 0.01% to 2% by weight of onium salt relative to the reaction mixture will be used.

The amount of chlorine used in the process according to the invention is essentially a function of the desired conversion rate of the phenolic compound (I).

In practice, most typically, chlorine is introduced by bubbling same into the reaction mixture. The pressure in the apparatus is therefore essentially equal or slightly higher than atmospheric pressure.

The chlorine may be used alone or be diluted with an inert gas, such as nitrogen for example. The presence of an inert gas makes it possible, if required, to increase the gaseous flow rate without simultaneously increasing the amount of chlorine introduced over the course of a given period of time.

The gaseous chlorine used in the present process may also be formed in situ, from hydrochloric acid, by addition of an oxidizing compound, such as, for example, hydrogen peroxide.

The temperature at which the process of the invention is carried out is usually less than or equal to 180° C. The lower limit is not critical. It is subject to the requirement of maintaining a liquid reaction mixture.

When conducting the reaction in the molten state, this lower temperature will vary according to the phenolic compound (I) subjected to chlorination. Therefore, when 2,6-dichlorophenol is chlorinated, a temperature at least equal to 65° C. will be required.

When conducting the reaction in a solvent medium, it will be possible for the temperature to be as low as, for example, 20° C.

However, the temperature will preferably range from 40° C. to 120° C., when the reaction is carried out in a solvent medium.

When conducting the reaction in the molten state, the preferred temperature will range from 40° to 120° C., except of course for the phenolic compounds having a melting point which is higher than 40° C., for which the preferred temperature zone will range from the melting point of the compounds to 120° C.

Among the phenolic compounds of formula (I) to which the process of the invention is applicable, especially representative are 2,6-dichlorophenol, 2,6-dimethoxyphenol, 2-chloro-6-methoxyphenol, 2-chloro-6-methylphenol, 2,6-di-chloro-3-methylphenol, 2,6-dichloro-3-methoxyphenol, 2-bromo-6-methoxyphenol, 2-chloro-6-nitrophenol and 2-chloro-6-acetamidophenol.

It is optionally possible to chlorinate mixtures of these phenolic compounds.

The process of the invention is particularly well adapted for the chlorination of 2,6-dichlorophenol to produce 2,4,6-trichlorophenol, because it makes it possible to obtain the latter compound while greatly limiting, generally to less than 3% by weight, the formation of undesirable by-products such as 2,4,5,6,6-pentachloro-2-cyclohexenone.

When the process of the invention is applied to 2,6-dichlorophenol, the latter may be especially obtained by chlorination, with gaseous chlorine, of 2-chlorophenol, in the presence of an organic cation such as previously defined.

It is therefore possible to thus produce 2,4,6-trichlorophenol by chlorination of 2-chlorophenol using gaseous chlorine in the presence of an organic cation, which will initially catalyze the chlorination of 2-chlorophenol to produce 2,6-dichlorophenol, and then the chlorination of the latter to produce 2,4,6-trichlorophenol.

It is also possible to conduct the chlorination of 2,6-dichlorophenol which has been prepared by chlorination of phenol with gaseous chlorine, in the presence of an organic cation such as previously defined.

It appears that it is also possible to apply the process of the invention to crude mixtures from the chlorination of phenol, which contain 2,6-dichlorophenol as well as 2,4-dichlorophenol, orthochlorophenol and possibly small amounts of parachlorophenol and phenol.

When it is applied to such industrial mixtures, the process of the invention makes it possible to obtain virtually only 2,4,6-trichlorophenol in excellent yields. Furthermore, practically very little 2,4,5-trichlorophenol is detected, this compound being undesirable.

The conditions described for the chlorination of the phenolic compounds of formula (I) and more particularly of 2,6-dichlorophenol, apply to the chlorination of phenol and/or 2-chlorophenol or of crude industrial mixtures from the chlorination of phenol, previously described.

In order to further illustrate the present invention and the advantages thereof, the following specific examples are given, it being understood that same are intended only as illustrative and in nowise limitative.

EXAMPLE 1

(i) 2,6-Dichlorophenol: 32.6 g (0.2 mol), and
(ii) tetrabutylammonium chloride: 0.33 g (i.e., 1% by weight relative to the 2,6-dichlorophenol),
were charged into a 200 cc glass reactor equipped with a stirrer, a dipping tube allowing the introduction of gaseous chlorine, a thermometer and fitted with a condenser.

The reaction mixture was heated under stirring at 70° C., and the gaseous chlorine was then introduced with a flow rate of 5 l/h over 54 min, which corresponded to an amount of chlorine of 200 mmol.

Upon completion of the reaction, the apparatus was flushed with a stream of nitrogen.

The reaction mass was analyzed by gas chromatography (GC) and by high-performance liquid chromatography (HPLC).

The following results were obtained:
(a) conversion rate (CR) of the 2,6-dichlorophenol:
(b) yield (Y) of 2,4,6-trichlorophenol relative to the converted 2,6-dichlorophenol: 97.1%
(c) Y of 2,3,4,6-tetrachlorophenol: 0.6%
(d) Y of 2,4,4,6-tetrachlorocyclohexadienone: 0.3%
(e) 2,4,5-trichlorophenol: 0.0003% by weight relative to the reaction mixture.

EXAMPLE 2

(i) 2,6-Dichlorophenol: 32.6 g (0.2 mol),
(ii) tetrachloroethylene: 612.5 g, and
(iii) tetrabutylammonium chloride: 6.45 g (20% by weight relative to the 2,6-dichlorophenol),
were charged into an apparatus similar to the one used in Example 1, but using a 1,000 cc reactor.

The reaction mixture was heated to 100° C., and, at that temperature, 4.48 liters of chlorine (0.2 mol) were introduced over 54 minutes.

Upon completion of the reaction, the test mixture was treated as in Example 1.

The following results were obtained:
(a) conversion rate (CR) of the 2,6-dichlorophenol: 85.9%
(b) yield (Y) of 2,4,6-trichlorophenol relative to the converted 2,6-dichlorophenol: 90.0%
(c) Y of 2,3,4,6-tetrachlorophenol: 1.2%.

EXAMPLE 3

(i) 42.66 g of a mixture of chlorophenols comprising:
orthochlorophenol: 0.09 g (0.22% by weight),
2,6-dichlorophenol: 10.08 g (23.63% by weight),
2,4-dichlorophenol: 18.05 g (42.32% by weight),
2,4,6-trichlorophenol: 11.21 g (26.28% by weight),
parachlorophenol: 0.57 g (1.35% by weight),
2,4,5-trichlorophenol: 0.0822% by weight,
(this mixture was a crude mixture emanating from the industrial chlorination of phenol, also comprising products which were not assayed), and
(ii) 0.42 g of benzyldimethylhexadecylammonium chloride, were charged into the apparatus described in Example 1.

The reaction mixture was heated to 70° C. under stirring, and then 4.85 liters of chlorine were introduced for 58 minutes, 14 seconds.

Upon completion of the reaction, the reaction mixture was treated and analyzed as in Example 1.

50.26 g of a mixture consisting of:
2,6-dichlorophenol: 0.23 g (0.46% by weight),
2,4-dichlorophenol: 0.05 g (0.10% by weight),
2,4,6-trichlorophenol: 46.91 g (93.33% by weight),
2,3,4,6-tetrachlorophenol: 1.26 g (2.51% by weight),
4,4,6-tetrachlorocyclohexadienone: 0.5 g (0.99% by weight),
2,4,5-trichlorophenol: 0.0019% by weight,
were obtained.

The essentially complete disappearance of the 2,4,5-trichlorophenol over the course of the chlorination in the presence of the quaternary ammonium salt was observed.

COMPARATIVE TEST A (i) 2,6-Dichlorophenol: 24.45 g (0.15 mol), and
(ii) isopropyl ether: 254 g,
were charged into an apparatus similar to the one used in Example 1, but using a 500 cc reactor.

The reaction mixture was heated to 70° C. under stirring, and, at this temperature, 3.36 liters of chlorine were introduced over 40 minutes.

Upon completion of the reaction, the test mixture was treated and analyzed as in Example 1.

The following results were obtained:
CR of the 2,6-dichlorophenol 0%.

COMPARATIVE TEST B (i) 2,6-Dichlorophenol: 24.45 g (0.15 mol), and
(ii) carbon tetrachloride 254 g,
were charged into an apparatus similar to- the one used in Example 1, but using a 500 cc reactor.

The reaction mixture was heated to 75° C. under stirring, and, at this temperature, 3.36 liters of chlorine were introduced over 40 minutes.

Upon completion of the reaction, the test mixture was treated and analyzed as in Example 1.

The following results were obtained:
CR of 2,6-dichlorophenol: 3%
Y of 2,4,6-trichlorophenol: 90%.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the selective chlorination of an ortho-substituted phenolic compound having the formula (I):

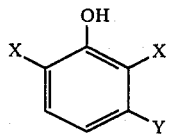

in which:
the symbols X, which may be identical or different, are each a chlorine atom, a bromine atom, a methyl or ethyl group, a methoxy or ethoxy group, an acetoxy group, an $NO_2$ group or an acylamino group having 1 to 4 carbon atoms, and the symbol Y is a hydrogen atom, a methyl or ethyl group, a methoxy or ethoxy group, comprising conducting said selective chlorination with gaseous chlorine, in the presence of a selectivity-enhancing effective amount of at least one organic cation comprising an onium ion derived from nitrogen, phosphorus, arsenic, sulfur, selenium, oxygen, carbon or iodine and which is coordinated with a hydrocarbon moiety.

2. The process as defined by claim 1, carried out in the molten state.

3. The process as defined by claim 1, carried out in a solvent medium.

4. The process as defined by claim 3, said solvent medium comprising an aliphatic ether, an aliphatic hydrocarbon, a chlorinated aliphatic hydrocarbon, a chlorobenzene or a bromobenzene, or a carboxylic acid.

5. The process as defined by claim 1, carried out in the presence of at least one organic cation of an onium salt, said organic cation having one of the following formulae:

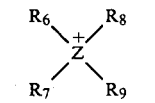 (II)

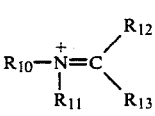 (III)

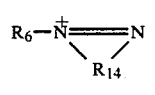 (III¹)

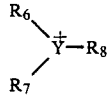 (IV)

 (V)

in which:
Z is N, P or As;
Y is S, O, Se, S=O or C;

$R_6$, $R_7$, $R_8$ and $R_9$, which may be identical or different, are each a straight or branched chain alkyl radical which has 1 to 16 carbon atoms and optionally substituted by one or more phenyl groups, hydroxyl groups, halogen atoms, nitro groups, alkoxy or alkoxycarbonyl groups, the alkoxy groups having 1 to 4 carbon atoms; a straight or branched chain alkenyl radical having 2 to 12 carbon atoms; an aryl radical which has 6 to 10 carbon atoms and optionally substituted by one or more alkyl groups having 1 to 4 carbon atoms, alkoxy groups, alkoxycarbonyl groups, the alkoxy radical having 1 to 4 carbon atoms, or halogen atoms, with the proviso that two of said radicals $R_6$ to $R_9$ may together form a straight or branched chain alkylene, alkenylene or alkadienylene radical having 3 to 6 carbon atoms;

$R_{10}$, $R_{11}$, $R_{12}$, $R_{13}$, which also may be identical or different, are each a straight or branched chain alkyl radical containing 1 to 4 carbon atoms, with the provisos
that the radicals $R_{12}$ and $R_{13}$ may together form an alkylene radical containing from 3 to 6 carbon atoms; and the radicals
$R_{11}$ and $R_{12}$ or $R_{11}$ and $R_{13}$ may together form an alkylene, alkenylene or alkadienylene radical containing 4 carbon atoms and, with the nitrogen atom, constitute a nitrogen-containing heterocycle;

$R_{14}$ is a divalent radical forming with the 2 nitrogen atoms a ring member which has 4 to 6 atoms and optionally containing one or more nitrogen, sulfur and/or oxygen atoms, with the proviso that such heterocycle may be substituted by one or more radicals $R_6$.

6. The process as defined by claim 5, wherein the anion associated with said at least one organic cation comprises $F^-$, $ClO^-_4$, $PF^-_6$, $BF^-_4$, $SnCl^-_6$, $SbCl^-_6$, $B(Ph)^-_4$, $PO^{3-}_4$, $HPO^{2-}_4$, $H_2PO^-_4$, $CH_3SO^-_3$, $Ph$-$SO^-_3$, $HSO^-_4$, $NO^-_3$, $SO^{2-}_4$, $Cl^-$, $Br^-$, $I^-$ or $OH^-$, with Ph denoting a phenyl radical.

7. The process as defined by claim 6, said anion comprising $PF^-_6$, $PO^{3-}_4$, $HPO^{2-}_4$, $H_2PO^-_4$, $CH_3SO^-_3$, $Ph$-$SO^-_3$, $NO^-_3$ $SO^{2-}_4$, $Cl^-$, $Br^-$ or $I^-$, with Ph denoting a phenyl radical.

8. The process as defined by claim 5, said at least one organic cation comprising a quaternary ammonium, a quaternary phosphonium, a sulfonium or an iodonium cation.

9. The process as defined by claim 5, wherein the organic cation is present in such an amount that the weight of the onium salt relative to the weight of the phenolic compound of formula (I) ranges from 0.005% to 25%.

10. The process as defined by claim 9, carried out in the presence of 0.015% to 5% by weight of the onium salt relative to the weight of the phenolic compound (I).

11. The process as defined by claim 10, carried out in the presence of 0.01% to 2% by weight of the onium salt relative to the weight of the reaction mixture.

12. The process as defined by claim 1 said phenolic compound having the formula (I) comprising 2,6-dimethoxyphenol, 2-chloro-6-methoxyphenol, 2-chloro-6-methylphenol, 2,6-dichloro-3-methylphenol, 2,6-chloro-3-methoxyphenol, 2-bromo-6-methoxyphenol, 2-chloro-6-nitrophenol or 2-chloro-6-acetamidophenol.

13. The process as defined by claim 12, said phenolic compound having the formula (I) comprising 2,6-dichlorophenol.

14. The process as defined by claim 1, carried out at a temperature of from 40° C. to 120° C.

15. The process as defined by claim 13, said 2,6-dichlorophenol having been prepared by chlorination of 2-chlorophenol, using gaseous chlorine, in the presence of such at least one organic cation.

16. The process as defined by claim 13, said 2,6-dichlorophenol having been prepared by chlorination of phenol, using gaseous chlorine, in the presence of such at least one organic cation.

17. The process as defined by claim 1, said phenolic compound having the formula (I) comprising admixture of 2,6-dichlorophenol, 2,4-dichlorophenol, orthochlorophenol and, optionally, minor amounts of parachlorophenol and phenol.

18. The process as defined by claim 14, carried out at a temperature ranging from the melting point of the phenolic compound to 120° C.

* * * * *